United States Patent [19]
Strohmeyer et al.

[11] Patent Number: 5,157,253
[45] Date of Patent: Oct. 20, 1992

[54] ENVELOPE REFLECTANCE METER EVALUATING PRINT CONTRAST

[75] Inventors: James J. Strohmeyer, Hampstead; Horace W. Weeks, Towson, both of Md.; Alan R. Bourque, Bridgeton, Mo.; M. Leighton Greenough, Rockville, Md.

[73] Assignee: Chamberlain MRC, Division of Duchossois Industries, Inc., Elmhurst, Ill.

[21] Appl. No.: 585,764

[22] Filed: Sep. 20, 1990

[51] Int. Cl.⁵ .......................... G01J 3/50; G06K 7/10
[52] U.S. Cl. .................................... 250/226; 250/568
[58] Field of Search ............... 209/580, 581, 582, 583, 209/584; 250/226, 223 R, 568, 239; 356/402, 407–408, 425; 235/462, 465

[56] References Cited

U.S. PATENT DOCUMENTS

| | | | |
|---|---|---|---|
| 3,867,039 | 2/1975 | Nelson | 209/582 |
| 3,933,094 | 1/1976 | Murphy et al. | 209/584 |
| 4,020,357 | 4/1977 | Punis | 250/568 |
| 4,360,798 | 11/1982 | Swartz et al. | 235/463 |
| 4,476,982 | 10/1984 | Paddock et al. | 209/582 |
| 4,606,660 | 8/1986 | Bradshaw et al. | 209/584 |
| 4,940,850 | 7/1990 | Satake | 209/582 |

FOREIGN PATENT DOCUMENTS 2924605  4/1980  Fed. Rep. of Germany ...... 209/582

*Primary Examiner*—David C. Nelms
*Assistant Examiner*—Michael Messinger
*Attorney, Agent, or Firm*—Lowe, Price, LeBlanc & Becker

[57] ABSTRACT

An envelope reflectance meter for evaluating the contrast between ink on a pre-printed envelope and the envelope itself and for calculating and displaying the print contrast ratio and the print reflectance difference is described. The device includes a portable housing having internally a pair of light sources which generate a reflected image of the envelope. The image passes through a lens, is reflected from a mirror, and is then displayed on a viewplate. An aperture is provided in the viewplate which passes a beam of light. The beam of light is then split and the two beams resulting analyzed for red content and green content. The analog signal produced is then converted to digital and the print contrast ratio and print reflectance difference calculated. A display is provided within the housing adjacent the viewplate whereby selectively the values for red light and for green light and comparisons between the readings for ink and the readings for the envelope are selectively displayed for an operator.

11 Claims, 3 Drawing Sheets

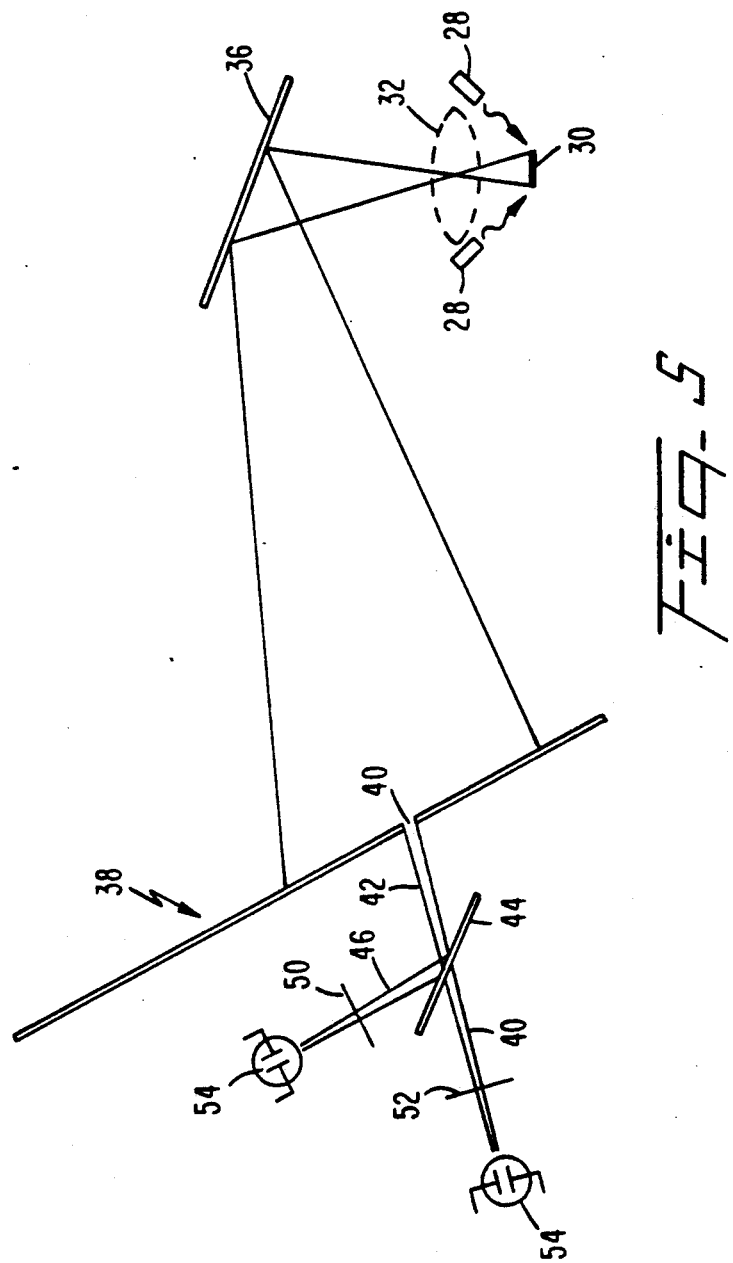

ENVELOPE REFLECTANCE METER EVALUATING PRINT CONTRAST

FIELD OF THE INVENTION

This invention relates to a meter for measuring light reflectance so that preprinted envelopes and packages can be evaluated as to whether they can be handled automatically by the U.S. Postal Services.

BACKGROUND OF THE INVENTION

The U.S. Postal Service uses primarily scanning apparatus to read coded information imprinted on envelopes and packages. In addition to the bar code scanner, the Postal Service also uses alphanumeric optical character readers. While these devices can read both letters and numerals, they also can read bar codes.

A basic requirement for this sensing apparatus is that there be at least a predetermined contrast between the envelope paper or background and the ink which constitutes the bar code or other information. The optimum condition would require the maximum reflectivity from the paper and the minimum reflectivity from the printed material thereon. The reflectance of the paper and of the ink are parameters which are used to calculate the print reflectance difference (PRD) and print contrast ratio (PCR). The PRD and the PCR for a piece of mail then must meet postal service standards or it will be unacceptable for automatic handling.

A laboratory spectrophotometer can be used to evaluate the reflectance of the paper and of the ink. Conventional laboratory spectrophotometers, however, are large pieces of equipment and, therefore, not portable. In addition, they are quite expensive in that they are intended normally to perform a variety of functions not necessary to or not related to the requirements for an envelope reflectance meter. In addition, a spectrophotometer will produce a reading of reflectance from the paper and reflectance from the ink. However, a spectrophotometer does not calculate the PRD and PCR required to evaluate the object against U.S. Postal Service standards. Therefore, the technician would have to manually calculate the standard values if using a laboratory spectrophotometer.

There is a portable unit available manufactured by Photographic Sciences, Inc. which will read reflectance and display the calculation of the PRD and PCR automatically. The device consists of two units interconnected by a cable, and the operator takes readings with a microscope-type eyepiece in one unit and the display is in the other unit.

There is, therefore, a need for a lightweight, portable device for use by the U.S. Postal Service for evaluating reflectance, which can be used by a relatively untrained operator, and which is accurate and does not require frequent calibrations.

SUMMARY OF THE INVENTION

It has been discovered that a portable, lightweight and relatively inexpensive envelope reflectance meter can be developed which in a single unit displays the PRD and PCR ratios. In addition, the device of this invention takes an analog reading converts it to digital and produces the necessary display in a real time fashion so that the operator can quickly take readings of reflectivity and contrast at high or low reflectivity areas such as where printing is smeared or splattered.

Accordingly, it is an object of this invention to provide an envelope reflectance meter in a single unit which is accurate and requires only infrequent calibrations. It is another object of this invention to provide an envelope reflectance meter which can be used by a relatively untrained operator and which displays in the viewing area the print contrast ratio and print reflectance difference with a continuous scan in a real time fashion.

It is yet another object of this invention to provide an envelope reflectance meter which utilizes two light sources to produce a single reflected beam which is then split and read for red and green content which are then displayed to the operator in response to the operator's activation of a predetermined control.

It is still another object of this invention to provide an envelope reflectance meter which has an internal calibration standard whereby the operator can calibrate the device, or which in the alternative can be automatically calibrated to produce a signal with an accuracy of plus or minus 1% of reflectance over the entire range of from 0 to 100% reflectance.

These and other objects will become readily apparent with reference to the drawings and following description wherein:

BRIEF DESCRIPTION OF THE DRAWINGS

FIG. 5 is a schematic of the optical arrangement of the meter of this invention.

DETAILED DESCRIPTION OF THE INVENTION

Figure 1:
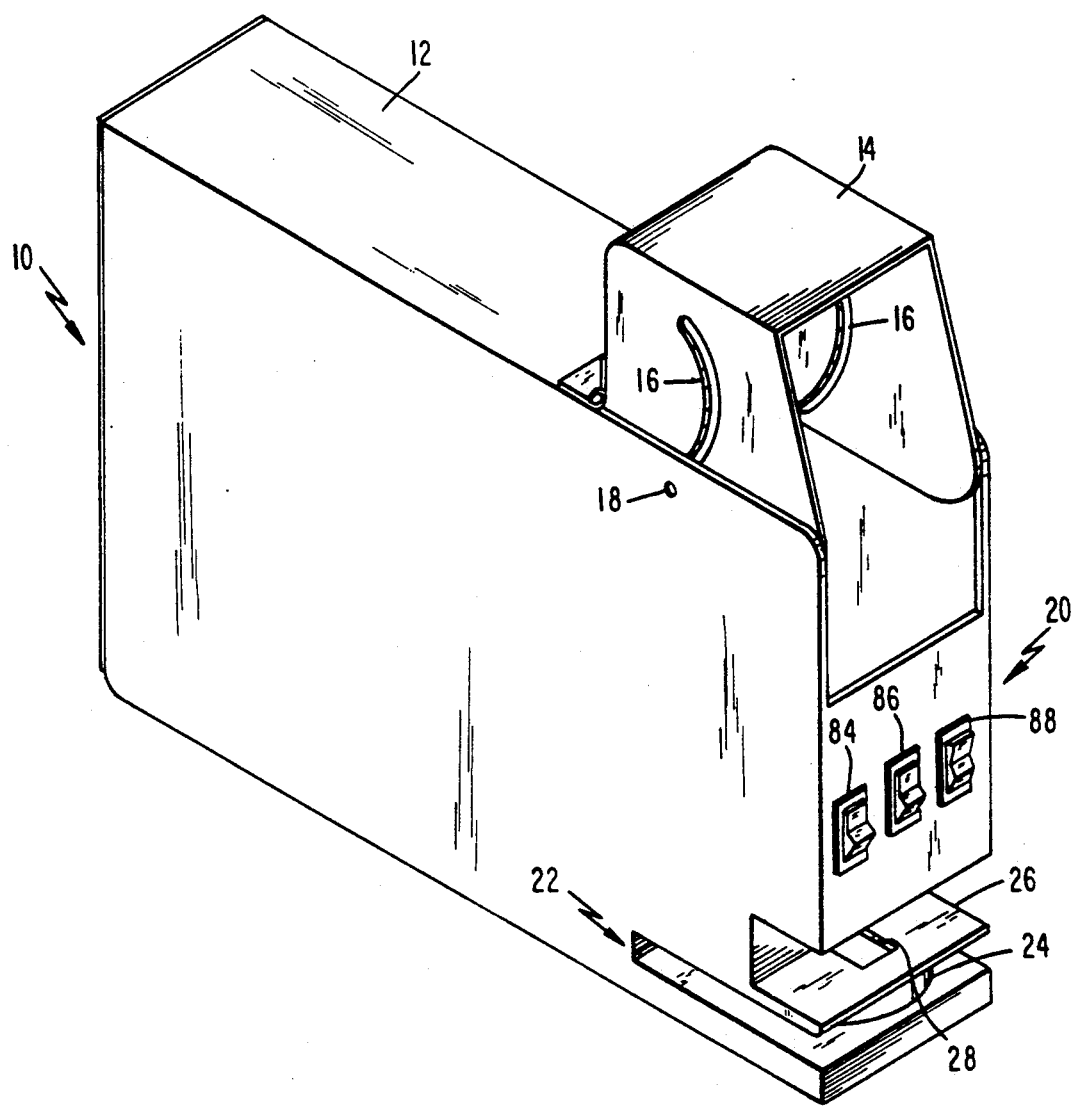
FIG. 1 is a perspective view of the envelope reflectance meter of this invention.
Figure 3:
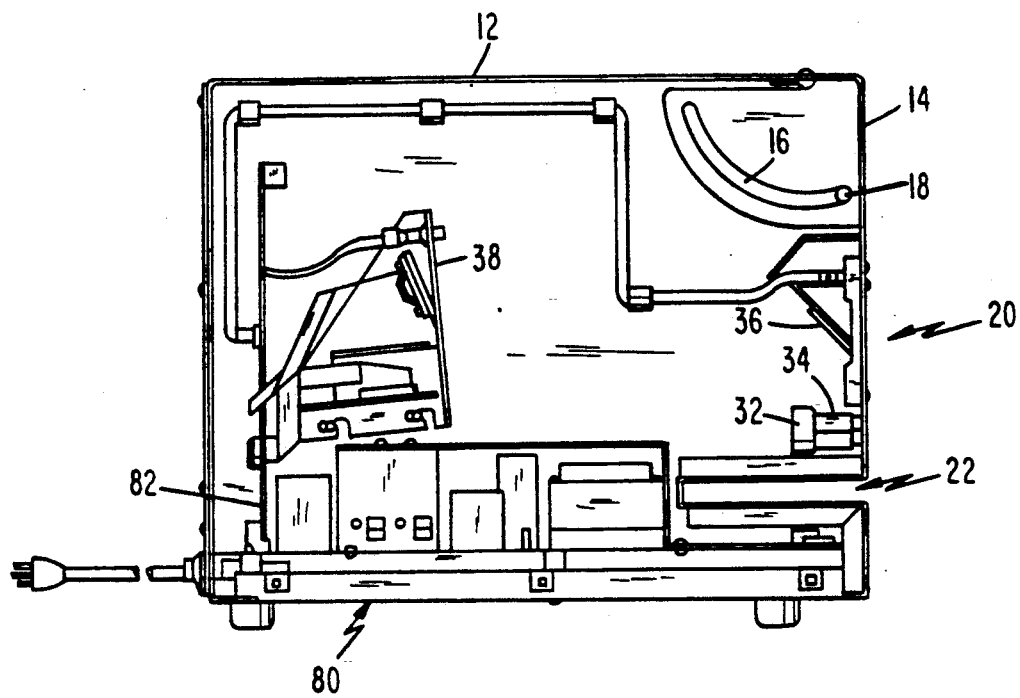
FIG. 3 is a side view of the device of FIG. 1 with one side removed.

With attention to the drawings and to FIGS. 1 and 3 in particular, the device of this invention 10 consists of a chassis 12 with a hood 14 rotatable along arcuate slots 16 wherein opposed buttons 18 ride from the open position of FIG. 1 to the closed position of FIG. 3. A control panel 20 is mounted below hood 14 as will be subsequently explained. Also below hood 14 is a slot 22 which receives an envelope or other article to be read and a spring loaded nylon retainer 24 holds the object against upper plate 26 which has a viewing slot 28 for the objective as will be subsequently explained.

As will be apparent, the embodiment of FIG. 3 differs from the embodiment in FIG. 1 in the absence of spring loaded nylon retainer 24. These two embodiments, however, function identically.

Figure 2:
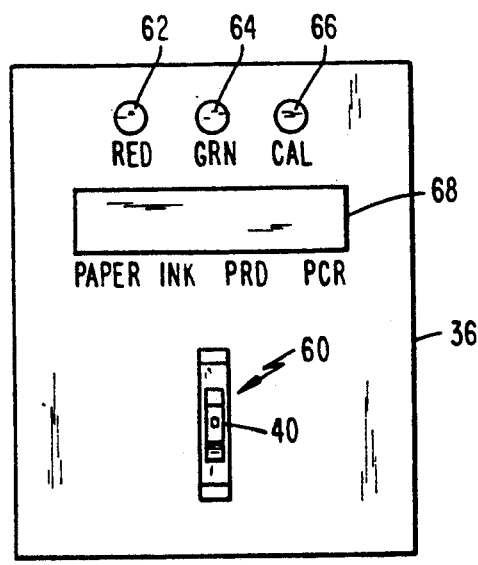
FIG. 2 is a front view of the reflectance meter viewplate.
Figure 4:
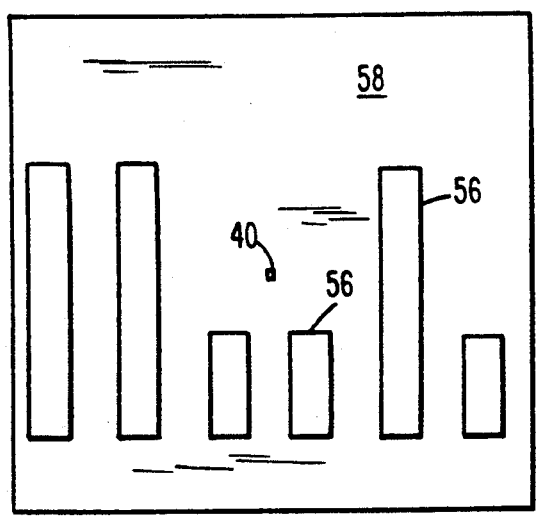
FIG. 4 is a front view of a bar code label viewed through the envelope reflectance meter.

With attention to FIGS. 5 and 3, two sources of light 28 direct light downwardly on the object to be read 30. The light is then reflected upwardly through a lens 32 mounted on block 34 to a mirror 36. Lens 32 preferably magnifies the image ten times. The image is reflected from mirror 36 onto viewplate 38 wherein a predetermined portion passes through an aperture 40. The beam of light 42 passing through the aperture 40 is then split by a beam splitter 44 and separate beams 46 and 48 pass through respectively red and green filters 50 and 52 to photodiodes 54 which convert the red and green beams to electrical energy in the conventional fashion. With attention to FIG. 4, there is a display similar to that which would be presented on the viewplate 38 of the reflected object which in this case is a bar code consisting of bars 56 which are of ink printed on an envelope background 58. Note aperture 40 in FIG. 4 which would be passing a beam of light for evaluation of the reflectance of the background paper. The reflectance of the ink in the bar code 56 would be read by manually moving the envelope until aperture 40 is aligned at the proper place on the image. With attention to FIG. 2, in order to assist in the alignment a reticle 60 is provided with aperture 40 at its center.

The display which the operator views indicates at light 62, 64 and 66 whether the reading displayed on the display 68 below is of the red beam, the green beam, or whether the machine 10 is in the calibration mode. As shown on display 68 then the portion thereof above "paper" or above "ink" would display the reflectance thereof and the portion above the letters "PRD" and "PCR" would reflect those calculations which are performed automatically as will be subsequently explained.

With attention to FIG. 5, it was discovered that a single light source incident to the envelope was not desirable with envelopes of coarse paper. The single light surface would illuminate pits in the surface of the paper. It was discovered, however, that two light sources at angles of 40 degrees to the paper surface eliminated this problem. In the preferred embodiment of this invention, two 1,000 foot-candle prefocused lamps are used which are directed at 40 degree angles to the surface and have an incident angle of 100 degrees between each other.

The preferred optical system includes a 24 mm, 1.6/f fixed focus objective lens. The aperture of the lens insures sufficient light capture to project an image of the envelope surface onto the viewplate 38. The viewplate in the preferred embodiment is placed at a distance of 250 mm from the lens and displacement achieves a lateral linear magnification of 10x. The mirror 36 is placed at a distance 60 mm from the objective lens.

Finally, the beam splitter 44, filters 50 and 52 and photodetectors 54 are all mounted in a single machined block directly behind the aperture stop 40 of the viewplate 38. This eliminates any periodic adjusting that might otherwise have to be performed to keep these components properly aligned.

Operation

The power supply 80 is located in the base of the device and is used to convert 115 VAC line voltage into a regulated DC voltage source for use by the lamps and a regulated DC power source for the reflectance meter electronics. The power supply resides in its own printed circuit board 83 which is separate from the control electronics. It is accessible through the base of the device.

The major component in the control electronics is preferably a Motorola 68HC11 microcontroller. This controller is an 8-bit microcontroller with four digital I/0 ports and a fifth port which is multiplexed to an internal analog to digital (A/D) converter.

The microcontroller transfers digital data between the various I/0 devices via a pair of 8-bit latches and a bidirectional databus transceiver. Address decoding is accomplished using a 3 of 8 decoder. Program memory, 8K $\times$ 8, is external to the microcontroller and resides in a 2764 EPROM device.

The display (See FIG. 2, 68) is an AND673-JO intelligent LCD display. This is a large scale integrated device which receives a command code and a sequence of data bytes from the microcontroller. This device then provides the proper timing and control signals to drive the individual segments of the LCD display.

As will be obvious to those skilled in the art, the foregoing electronics are provided as examples and not intended to be limitive.

As noted above, there are two photodetectors for the two channels, red and green. Signals are amplified by conventional amplifiers which have adjustment potentiometers to adjust for both gain and offset. These are set to provide approximately a 0 to 4.6 V dynamic range for each channel corresponding to 0 reflectance and to 100% reflectance. The output of these amplifiers is then fed directly into the multiplexed inputs of the analog to digital converter. A precision voltage reference is used to set the range on the analog to digital converter. The range will be set at 0 to 4.6 volts to provide maximum precision during the conversion process. The 8-bit internal analog to digital converter provides a measurement accuracy exceeding 0.5%. The control electronics reside on a single printed circuit board 82 on the back of the device. It also is placed within close proximity to the photodetectors 54 to reduce the possibility of inductive coupling of the sensor lines due to lengthy wire runs.

With attention to FIG. 1, the device of this invention has three rocker-type control switches located on the front 20 of the unit. The first control switch 88 is a three-position switch used by the operator to take readings of the ink and paper reflectances. When the upper portion of switch 88 is fully depressed, the controller will identify reflectance readings as for paper. When the lower portion is fully depressed, ink readings will be identified. When taking a reading on ink reflectance, the operator aligns the area to be read within the reticle 60 and the reference value for the region under scrutiny will be displayed on the ink reflectance display on display 68 on a real time basis. Setting the switch 88 in the middle position shown in FIG. 1 will result in locking this value into the memory. To take a reading for paper, the switch is depressed to the paper side, and the procedure repeated. The advantage of this type of control is that a single paper reading can be taken followed by a succession of ink readings, and the meter of this invention will display the PRD and PCR for each individual ink sample as compared to the one paper sample. Switch 84 identifies readings to be taken from, respectively, the green channel or the red channel. Fully depressing the upper portion of switch 84 will cause red channel readings to be displayed. Fully depressing the lower portion will cause green channel readings to be displayed. Although the meter of this invention reads both channels simultaneously and automatically calculates the PRD and PCR, only one channel can be read out on the display at one time. Finally, switch 86 distinguishes between a calibrate mode when the lower portion is depressed and an operate mode when the upper portion is depressed. Switches 84 and 86 do not have middle positions as shown in switch 88.

The display 68 itself is a single 15-digit numeric LCD display broken down into four separate display sections with nonilluminated digits in between to give the appearance of four individual displays. Each display is capable of showing a maximum of three digits and the displays are labelled from left to right, Paper, Ink, PRD and PCR. As noted above, the "Paper" and "Ink" displays are the reflectance and whether it is the green channel or the red channel will be determined by which portion of switch 84 is depressed. That will also be displayed at either 62 or 64 on the viewing plate 38.

As previously indicated, the reflectance displays are updated in real time provided that the sample switch is depressed to the right setting. When the sample switch 88 is released, the last reflectance value displayed is locked into the meter and will be used to calculate the PRD and PCR values. The PRD and PCR values displayed will be updated whenever a new reflectance value is entered. By switching the spectrum select switch 84 from one setting to the other, the display will change to show the values obtained under the different spectrum.

Calibration of the device is achieved by using a black standard and a white standard. Preferably the black standard has a reflectivity of less than 5% and the white standard has a reflectivity exceeding 90%. The operator can check calibration by depressing the rocker switch 88 to the paper mode and positioning the white standard beneath the objective lens. Then the switch 88 is depressed to the ink mode and the black standard is read. In a preferred embodiment of this invention, the device can be calibrated by depressing switch 86 to the calibrate mode and adjusting four trim potentiometers which affect the gain and offset of the operational amplifiers in a conventional fashion.

The device also incorporates an auto calibration mode. The switch 86 is depressed to the calibrate mode and a special indicator light 66 illuminates on the display screen indicating that the unit is in a calibration mode. The reflectance values for the two standards are read by the microcontroller from a series of a preset switches on the control electronics board. When the operator takes readings for the two standards, the meter compares these values against preset values and automatically adjusts the dynamic range of the unit to compensate for any differences. This will eliminate the need for manual adjustment of trim potentiometers under normal circumstances. In addition, a warning system is built in to indicate if the automatic adjustment deviates more than one percent from the true reflectance whereupon the calibrate indicator light 66 would flash.

The device of this invention is intended to insure accurate, stable operation and to be simple in design to assure reliability and contain costs.

In summary, an envelope reflectance meter has been described which is lightweight and reliable and uncomplicated to operate. The meter projects an image of an envelope caused by twin light sources through a lens and mirror onto a viewplate where it is magnified 10x. An aperture on the viewplate is provided and light passing through the aperture is split, both beams filtered, and a continuous reading of the red light from one beam and green light from another beam is provided by twin photodetectors. The analog reading from the photodetectors is then converted to digital and fed into a microprocessor.

In order to operate the device of this invention, the operator turns one switch to an on position, sets another switch for a reading for either paper or ink and then views the viewplate. The device can be set to produce the reflectance from the red beam or the green beam and automatically calculate from the envelope reflectance the print reflectance difference and the print contrast ratio. In addition, a single initial reading of the envelope may be taken and a number of subsequent readings on ink taken and each then compared to the original envelope reading. The ratios are then produced without taking additional envelope readings with each ink reading. Furthermore, the device is capable of a continuous scan with a real time printout of the parameters and ratios.

The invention may be embodied in other specified forms without departing from the spirit or essential characteristics thereto. The present embodiments are therefore to be considered in all respects as illustrative and not restrictive, the scope of the invention being indicated by the appended claims rather than by the foregoing description, and all changes which may come within the meaning and range of equivalency of the claims are therefore intended to be embraced therein.

We claim:

1. A reflectance meter for evaluating the contrast between an ink inscription and a background object bearing the inscription and for calculating and displaying the print contrast ratio and the print reflectance difference thereof comprising:

a housing having a view opening whereby an operator may view the interior of said housing and a slot therebelow for insertion of the printed object to be evaluated;

a pair of light sources disposed within said housing, each source positioned to direct a beam of light downwardly onto said object at an incident angle of 40 degrees with an incident angle between the beams of 100 degrees;

lens means for receiving a reflected image of the object, magnifying and transmitting said magnified image;

mirror means disposed below the view opening for reflecting the image from the lens;

a view plate having an aperture therethrough, said mirror reflecting the image from the lens onto said view plate so that a beam of light passes through the aperture;

optical analysis means mounted on a block immediately behind the aperture for intercepting the beam of light and generating a first electrical signal proportional to the red light content of said beam and a second signal proportional to green light content whereby said signals can be independently processed to calculate the values of the red light reflectance, green light reflectance and the print contrast ratio and print reflectance difference thereof; and display means disposed within said housing adjacent said view plate for selectively displaying the red light values or the green light values.

2. The meter of claim 1 wherein said optical analysis means include a beam splitter means for splitting the beam passing through the aperture into two beams, respectively, a filter passing only red light and a photodiode therefor and a filter passing only green light and a photodiode therefor one of each filter and photodiode receiving one of said split beams for analysis.

3. The meter of claim 1 wherein said viewplate further includes a reticle surrounding the aperture to assist in aligning the reflected image and the aperture.

4. The meter of claim 1 wherein said lens magnifies the image 10 times.

5. The meter of claim 1 further comprising a hood slidably mounted on said housing over the viewing opening slidably between a closed position covering the opening and an open position.

6. The meter of claim 1 further comprising a control panel mounted on the exterior of said housing including selector switch coupled to said display means for selecting red or green values to be displayed and for identifying whether the values are based on an image of the background or the ink printing thereon.

7. The meter of claim 1 wherein said light sources are two 1000 foot-candle prefocused lamps.

8. The meter of claim 1 wherein said mirror means is disposed 60 mm from said lens means and said view plate is disposed 250 mm from said lens means in the direction the image beam travels.

9. Method for evaluating the contrast between the print on a preprinted object and the background of the object comprising the steps of:

providing a housing having a view port and a means for mounting the object;

directing two beams of light on a portion of the object to be evaluated each disposed at a 40 degree angle thereto;

enlarging the image produced and projecting the image on a screen having an aperture to produce a beam of light therethrough;

splitting said beam of light into two beams and projecting each through a screen passing respectively red and green light and then onto a photodiode to produce an electrical signal proportional to the intensity thereof;

evaluating the intensity of light projected in the red and green spectrum against predetermined standards as a measure of contrast; and displaying the evaluation within the housing for viewing through the view port.

10. The method of claim 9 wherein the preprinted object is a piece of mail and the print is a bar code.

11. The method of claim 9 wherein the object is a preprinted envelope and the print is the address.

* * * * *